United States Patent [19]

Bissonette et al.

[11] Patent Number: 4,753,653
[45] Date of Patent: Jun. 28, 1988

[54] FOLDABLE BIFOCAL INTRAOCULAR LENS

[75] Inventors: Noel G. Bissonette, Richfield; Thomas M. Heyman, Prior Lake; Harold H. Hogan, Brooklyn Park, all of Minn.

[73] Assignee: Precision-Cosmet Co., Inc., Minneapolis, Minn.

[21] Appl. No.: 926,432

[22] Filed: Nov. 3, 1986

[51] Int. Cl.[4] .................................. A61F 2/16
[52] U.S. Cl. ........................................ 623/6
[58] Field of Search ................ 623/6; 351/161, 168

[56] References Cited

U.S. PATENT DOCUMENTS

| 3,034,403 | 5/1962 | Neefe | 623/6 |
|---|---|---|---|
| 3,270,099 | 8/1966 | Camp . | |
| 3,794,414 | 2/1974 | Wesley | 351/161 |
| 4,010,496 | 3/1977 | Neefe | 623/6 |
| 4,343,050 | 8/1982 | Kelman | 623/6 |
| 4,373,218 | 2/1983 | Schachar | 623/6 |
| 4,402,579 | 9/1983 | Poler | 623/6 |
| 4,435,856 | 3/1984 | L'Esparance | 623/6 |
| 4,450,593 | 5/1984 | Poler | 623/6 |
| 4,451,938 | 6/1984 | Kelman | 623/6 |
| 4,504,982 | 3/1985 | Burk | 623/6 |
| 4,512,040 | 4/1985 | McClure | 623/6 |
| 4,525,043 | 6/1985 | Bronstein | 351/160 R |
| 4,573,998 | 3/1986 | Mazzocco | 623/6 |
| 4,605,409 | 8/1986 | Kelman | 623/6 |
| 4,619,657 | 10/1986 | Keates et al. | 623/6 |
| 4,636,211 | 1/1987 | Nielsen et al. | 623/6 |
| 4,657,546 | 4/1987 | Shearing | 623/6 |
| 4,664,665 | 5/1987 | Reuss et al. | 623/6 |

FOREIGN PATENT DOCUMENTS

| 0099641 | 2/1984 | European Pat. Off. | 623/6 |
|---|---|---|---|
| 0174917 | 3/1986 | European Pat. Off. . | |
| 39-27282 | 11/1964 | Japan | 351/161 |
| WO86/03961 | 7/1986 | PCT Int'l Appl. | 623/6 |

OTHER PUBLICATIONS

Business Week, Feb. 10, 1986, "Bifocal Contact Lenses Without a Pain in the Neck".
Opthalmology Times, May 1, 1986, vol. II, No. 9, "Bifocal IOL Design Offers Equal Vision", James McHenry Nielsen, M.D.

Primary Examiner—Ronald L. Frinks
Attorney, Agent, or Firm—Merchant, Gould, Smith, Edell, Welter & Schmidt

[57] ABSTRACT

A bifocal intraocular lens (20) for use as an artificial lens implant is disclosed. The bifocal intraocular lens (20) includes a lens body (21) having a chord (20b) and also having first and second relatively rigid members (24) and (30). The first section (24) is positioned on one side of the chord (20b) and the second section (30) is positioned on the other side of the chord (20b). The first section (24) has a focal length and the second section (30) has a focal length different from the focal length of the first section (24). Three embodiments of the bifocal intraocular lens (20, 50 and 80) are disclosed.

18 Claims, 3 Drawing Sheets

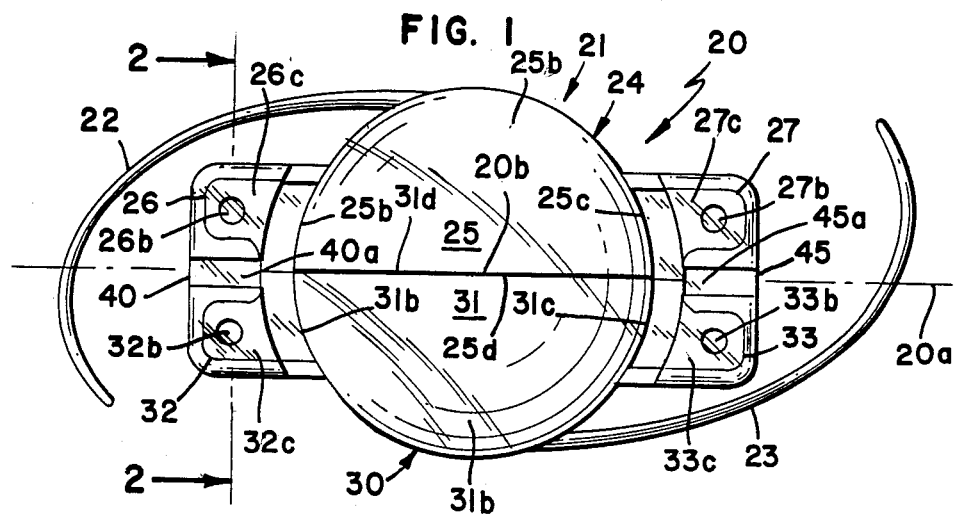
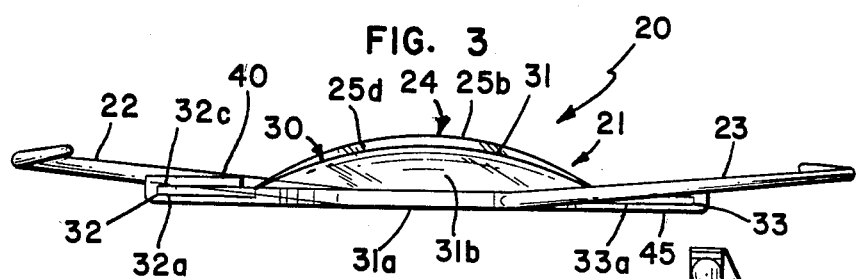
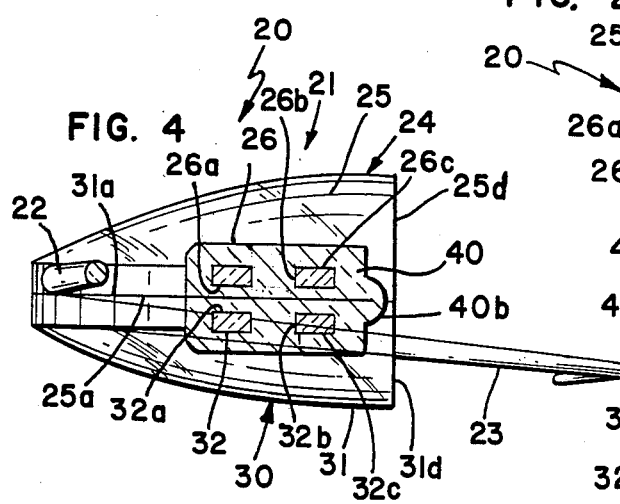
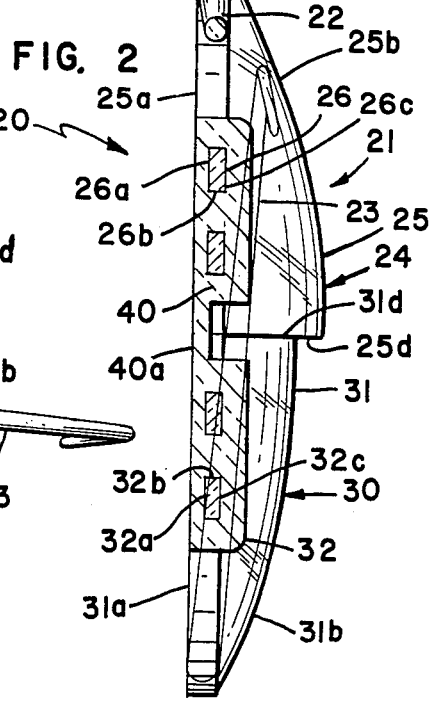

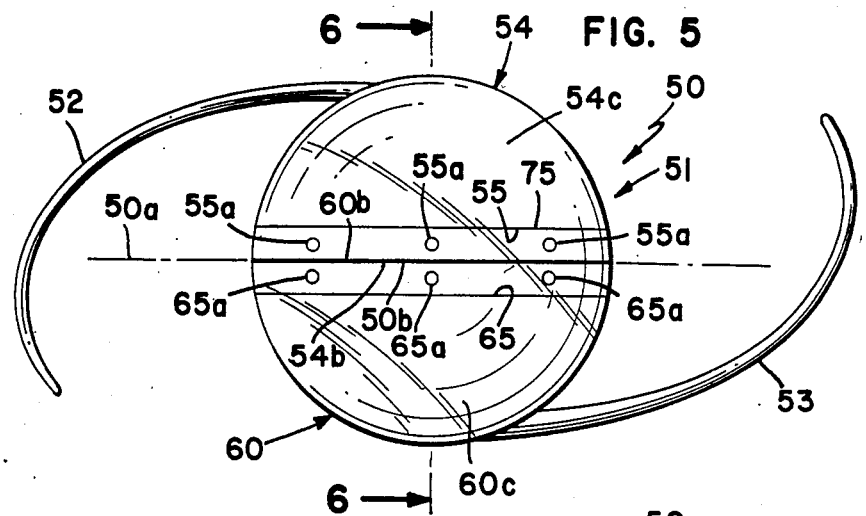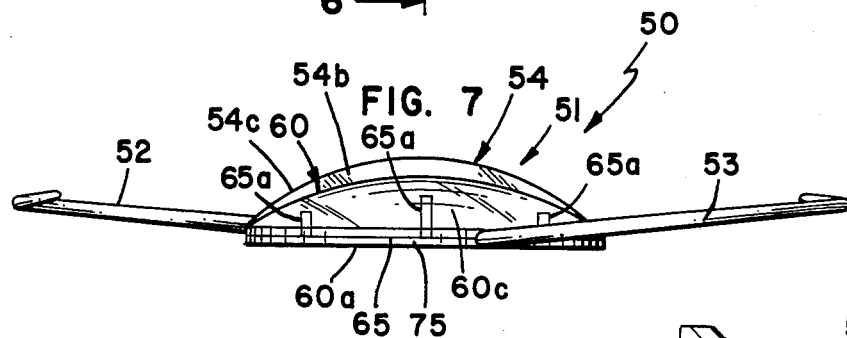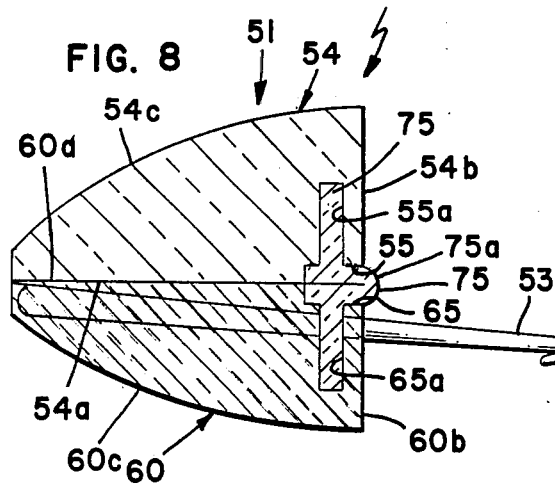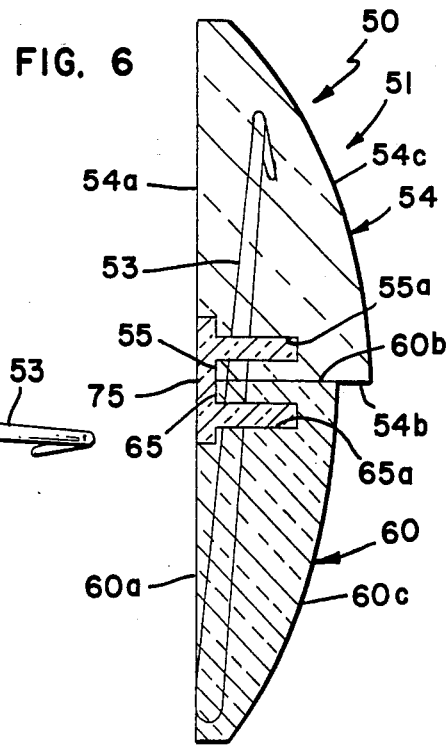

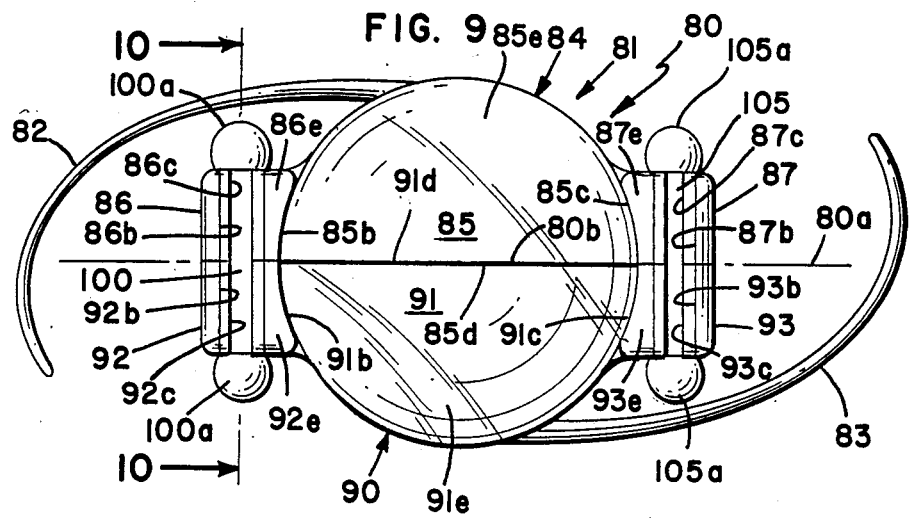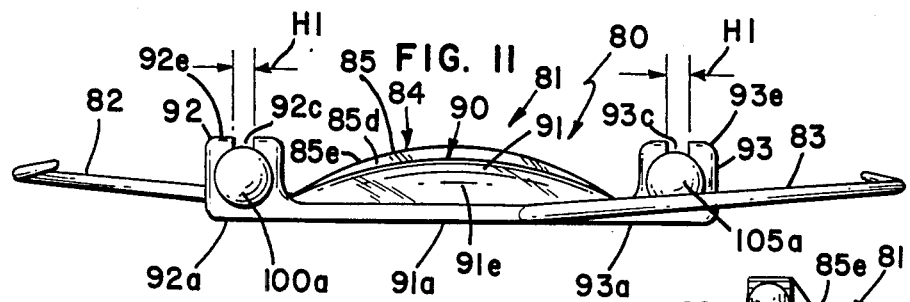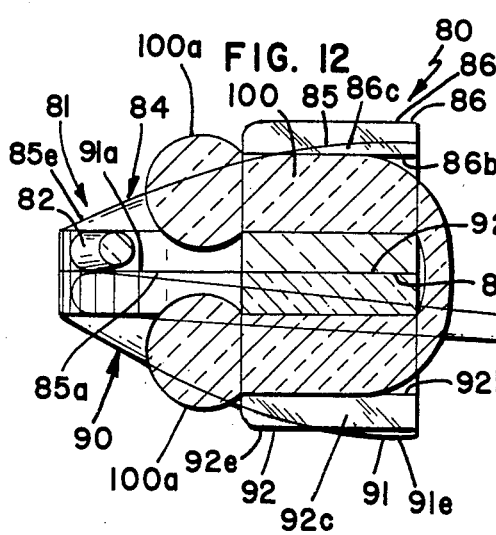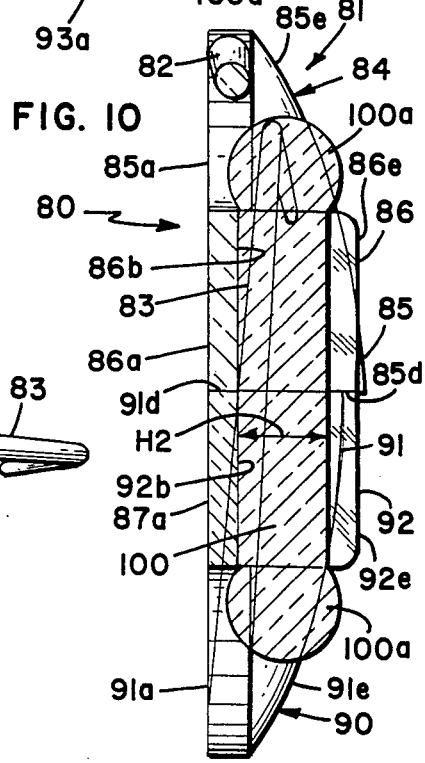

FOLDABLE BIFOCAL INTRAOCULAR LENS

BACKGROUND OF THE INVENTION

1. Field of the Invention

The present invention is generally directed to a foldable bifocal intraocular lens during insertion in the eye may be made smaller than the width when implanted, thereby requiring a smaller incision in the cornea than is now the case for implantation, and more particularly to an improved foldable lens having a resilient means which, once inserted and released, returns the lens to an operational configuration without further manipulation.

2. Description of the Prior Art

Many different types of synthetic intraocular lens structures have been developed to replace the natural lens of the human eye after lens removal during cataract surgery. In such operations, an opening or incision is made in the cornea and in the anterior surface of the capsular bag. The damaged lens tissue is removed by means of a vacuum tool resulting in loss of vision to the affected patient. In order to restore normal or correctable vision, a variety of lens structures have been developed which are designed to be affixed in the intraocular space of the eye. Such structures commonly comprise a centrally positioned lens and a plurality of appendages attached to the lens which function to position and secure the lens in front of or just behind the pupil.

The artificial lens is formed from an optically clear substance and shaped so as to focus impinging light onto the retina of the eye. Such lenses are commonly optically formed to be plano-convex, convex-plano, meniscus or bi-convex. The appendages attached to the lens typically comprise flexible legs of resilient plastic or metal fibers which are designed to make contact with appropriate structure in the interior of the eye.

One commonly employed type of intraocular lens structure is designed to position the lens in the anterior chamber of the eye just in front of the pupil. A structure of this type is disclosed, for example, by Kelman (U.S. Pat. No. 4,451,938). Another commonly employed type of intraocular lens structure is designed to position the lens in the posterior chamber of the eye just in back of the pupil. Devices of this type are disclosed by Faulkner (U.S. Pat. No. 4,366,582) and Shearing (U.S. Pat. No. 4,159,546). Streck (U.S. Pat. No. 4,361,913) discloses a lens which is indicated for possible use in either the anterior or posterior chambers.

Each of the structures mentioned above, except that of Kelman, is comprised of a single element lens with a plurality of haptics or positioned-fixation members attached to the lens. The lenses ordinarily have a circular perimeter. Thus, the incision in the cornea of the eye must be at least as long as the diameter of the lens. It is clear that the longer the incision, the greater will be the trauma to the eye and the longer will be the recovery time. Furthermore, since cataract surgery is usually performed on older patients, the general health of the patient may make it exceedingly important to keep the incision as short as possible. With this in mind, Kelman discloses in U.S. Pat. No. 4,451,938 an intraocular lens which is separable into two body portions. Each body portion is inserted separately through the cornea and the lens is then reassembled inside the eye during emplacement. Such lens structure certainly leads to the necessity for a shorter incision in the cornea than would otherwise be the case. The Kelman device, however, leads to delicate manipulation of the parts within the eye in order to reassemble the intraocular lens.

European Patent Application No. 83303414.3 by Kelman discloses an intraocular lens which may be inserted into an eye through a smaller incision. The optic is deformable by either folding a flexible optic lens body or by hinging a lens body. When hinging action is utilized, it is necessary for the hinges to be manually returned to their operational configuration after the lens has been inserted into the eye. The present invention addresses the problem of keeping the incision as short as possible in another way and also provides for a bifocal intraocular lens.

SUMMARY OF THE INVENTION

The present invention is a bifocal intraocular lens adapted for use as an artificial lens implant. The intraocular lens includes an optical lens body having a chord and having separate first and second relatively rigid circular segment sections. The first section is positioned on one side of the chord and the second section is positioned on the other side of the chord. The first section has a focal length and the second section has a focal length which is different from the focal length of the first section.

In one embodiment, the bifocal intraocular lens includes an optical lens body having a chord and having separate first and second relatively rigid circular segment sections. The first section is positioned on one side of the chord and the second section is positioned on the other side of the chord. The first section has a focal length and the second section has a focal length different from the focal length of the first section. The first section has a central portion and an outwardly extending flange portion. These central and flange portions have bottom surfaces. The flange portion of the first section has a first component cooperatively connected to the first end of the central portion and a second component cooperatively connected to the second end of the central portion. The second section has a central portion and an outwardly extending flange portion. The central and flange portions have bottom surfaces. The flange portion of the second section has the first component cooperatively connected to the first end of the central portion and a second portion cooperatively connected to the second end of the central portion.

In another embodiment, the intraocular lens has an optical lens body having a chord and having separate first and second relatively rigid circular segment sections. The first and second sections having bottom surfaces and adjacent edge surfaces. The first section is positioned on one side of the chord and the second section on the other side of the chord. The first section has a focal length and the second section has a focal length different from the focal length of the first section. The first section has a first recess in its bottom surface proximate its adjacent edge surface and the second section has a second recess in its bottom surface proximate its adjacent edge surface.

In still another embodiment of the present invention a bifocal intraocular lens has an optical lens body having a chord and having separate first and second relatively rigid circular segment sections. The first section is positioned on one side of the chord and the second section is positioned on the other side of the chord. The first section has a focal length and the second section has a focal length different from the focal length of the first section. The first section has a central portion having first and second ends and a first flange portion cooperatively connected to the first end and a second flange portion cooperatively connected to the second end. The second section has a central portion having first and second ends and a third flange portion cooperatively connected to the first end and a fourth flange portion cooperatively connected to the second end. Each of the flange portions have a bore. The bore of the first flange portion is in general alignment with the bore of the third flange portion and the bore of the second flange portion is in general alignment with the bore of the fourth flange portion when in an operational configuration.

BRIEF DESCRIPTION OF THE DRAWINGS

FIG. 1 is a top plan view of an intraocular lens in accordance with the present invention;

FIG. 2 is a cross-sectional view, taken along the lines 2—2 of FIG. 1;

FIG. 3 is a side view of the lens of FIG. 1;

FIG. 4 is a cross-sectional view of FIG. 2 shown in a folded position;

FIG. 5 is a top plan view of another embodiment of an intraocular lens in accordance with the present invention;

FIG. 6 is a cross-sectional view, taken along the lines 6—6 of FIG. 5;

FIG. 7 is a side view of the lens of FIG. 5;

FIG. 8 shows the cross-sectional view of FIG. 6 in a folded position;

FIG. 9 is a top plan view of still another embodiment of an intraocular lens in accordance with the present invention;

FIG. 10 is a cross-sectional view, taken along the lines 10—10 of FIG. 9;

FIG. 11 is a side view of the lens of FIG. 9;

FIG. 12 shows the cross-sectional view of FIG. 10 in a folded position.

DETAILED DESCRIPTION OF THE INVENTION

Referring to the drawings, wherein like numerals represent like parts throughout the several views, an intraocular lens, designated generally as 20, is shown in FIGS. 1 through 4. The intraocular lens 20 is a preferred embodiment of our invention and has an axis 20a and includes an intraocular lens body, generally designated as 21, and two haptic members 22 and 23. The haptic members 22 and 23 are cooperatively connected to the lens body 21 by means well known in the art. The lens body 21 includes a first section, generally designated as 24 and a second section, generally designated as 30. The first section 24 includes an optical region or central portion 25, having a planar bottom surface 25a and a convex upper surface 25b. The first section 24 also has a first section flange having a first component 26, having a planar bottom surface 26a and a planar upper surface 26c, cooperatively connected to the first end 25b of the central portion 25 and a second component 27, having a planar bottom surface not seen, but similar to surface 26a and a planar upper surface 27c, cooperatively connected to the second end 25c of the central portion 25. The first component 26 and second component 27 have a width less than the width of the central portion 25 and are connected to the central portion 25 at opposite ends and on one side of the axis 20a. The second section 30 includes an optical region or central region 31 having a planar bottom surface 31a and a convex upper surface 31b. The second section flange, which is cooperatively connected to the central section 31 has a first component 32, having a planar bottom surface 32a and a planar upper surface 32c, which is cooperatively connected to the first end 31b of central section 31 and a second component 33, having a planar bottom surface 33a and a planar upper surface 33c, is cooperatively connected to the second end 31c of central section 31. The first component 32 and second component 33 have a width less than the width of the central portion 31 and are connected at opposite ends and on one side of the axis 20a, opposite components 26 and 27. The central portion 25 has an adjacent edge surface 25d normal to the bottom surface 25a which, when in an operational configuration, is adjacent the adjacent edge surface 31d of the central section 31. The adjacent edge surface 31d is normal to the bottom surface 31a. In a preferred embodiment, the second section 30 is a mirror image of first section 24 and cross-sectional views taken through the second components 27 and 33 would be the mirror image of the cross-sectional views taken through the first components 26 and 32 as shown in FIGS. 2 and 4. The central portions 25 and 31 are relatively rigid and are not foldable.

In a preferred embodiment, the haptic member 22, central portion 25 and first and second flange components 26 and 27 are formed as an integral one-piece structure by a compression molding and machining process. However, it will also be appreciated that it may also be produced by other suitable methods such as injection molding and lathing. Similarly, the haptic member 23, central portion 31 and the first and second flange components 32 and 33 are formed as an integral one-piece structure by a compression molding and machining process. However, it will be appreciated that the first section 24 and the second section 30 may also be produced by other suitable methods such as injection molding or lathing. The first section 24 and second section 30 are made of a biologically tolerable and optically suitable material such as polymethylmathacrylate (PMMA). The haptic members 22 and 23 may be made of a flexible, compressible, resilient material such as PMMA or polypropylene, or other materials as well known in the art.

The flange components 26, 27, 32 and 33 are resiliently cooperatively connected, as will be more fully described hereafter, such that the first section 24 is foldable with respect to the second section 30, wherein the lens body 21 may be folded from an operational configuration, as shown in FIGS. 1 and 3, to a smaller insertion configuration, as shown in FIG. 4, making implantation possible through a smaller cut in the cornea of the eye than would otherwise be possible and after insertion and upon release of the resilient connecting means the lens body 21 returns to the operational configuration without further manipulation.

It is understood that the flange components 26, 27, 32 and 33 may be of other configurations than that shown in FIGS. 1 through 4. However, in a preferred embodiment, as shown in FIGS. 1 through 4, the flange components 26, 27, 32 and 33 are cooperatively connected to their respective sections 24 and 30 at an outer distance which is less than one half of the radius of the central portions 25 and 31. The flange portions 26, 27, 32 and 33 do not extend, at their outer ends, to the axis 20a. Further, the flange components 26, 27, 32 and 33 each have an aperture 26b, 27b, 32b and 33b, respectively which extends through the flange components.

To cooperatively connect the first section 24 to the second section 30, the sections 24 and 30 are placed such that the adjacent edge surfaces 25d and 31d are adjacent and mating. They are then placed in a suitable fixture which has a mold to form the resilient, foldable hinges 40 and 45. One suitable foldable, flexible, resilient material that may be utilized is silicone rubber, such as Silastic 382 medical grade elastomer by Dow Corning. The uncured rubber, along with its catalyst, is injected into the mold and cures to the shape that encapsulates the flanges 26, 27, 32 and 33, as shown in the drawings, in approximately 20 minutes. The molded rubber not only encapsulates the flanges 26, 27, 32 and 33 but also fills the apertures 26b, 27b, 32b and 33b, thereby more firmly and positively connecting the hinges 40 and 45 to the flanges. It is understood that other suitable foldable, flexible, resilient materials may be used. A full cure will be effected in approximately 24 hours. Preferably, the shape of the hinges 40 and 45 are mirror images of each other. The bottom surfaces of the components 26, 27, 32 and 33 are positioned above the bottom surfaces 25a and 31a such that when the hinges 40 and 45 are molded the bottom of the hinges 40 and 45 are coplanar with the bottom surfaces 25a and 31a. Further, the hinges 40 and 45 do not extend above the convex surfaces 25b and 31b respectively, thereby having a profile less than that of the central portions 25 and 31 respectively and not requiring the incision for implanting to be larger than that required for the central portions 25 and 31. The hinges 40 and 45 have an area of reduced thickness proximate a central region 40a and 45a. This is in part possible since the flange sections 26, 27, 32 and 33 do not extend to the axis 20a.

When implanting the intraocular lens 20 into the eye, the first section 24 is folded in a position overlying the second section 30, as shown in FIG. 4. When in the folded position, the adjacent edge surfaces 25d and 31d are coplanar and the bottom surfaces 25a and 31a are in an overlying relationship to one another. This enables the lens to be implanted through a smaller cut in the cornea of the eye than would otherwise be possible. After the lens 20 is inserted into the cornea of the eye, it may be released and the resilient hinges 40 and 45 return the lens 20 to its operational configuration, as shown in FIGS. 1 and 3, without further manipulation. Because of the resilient nature of the hinges 40 and 45, the first section 24 and second section 30 will move from the insertion configuration as shown in FIG. 4 to the operational configuration as shown in FIGS. 1 and 3. When in the operational configuration, the bottom surfaces 25a and 31a are coplanar and also coplanar with the bottom surfaces of the hinges 40 and 45. The eye will not see the line created by the adjacent surfaces 25d and 31d. It is believed that the line will not be seen because of the fact that the sharp image created by the remainder of the central portions 25 and 31 will overpower the blurred edge created by the adjacent surfaces 25d and 31d.

When in the insertion configuration as shown in FIG. 4, the hinges 40 and 45 will be bent along their central regions 40a and 45a with that area of reduced thickness creating the circular protrusion 40b. A similar protrusion, not shown, is created when the hinge 45 is folded over on top of itself when in the postion as shown in FIG. 4 for the first hinge 40.

The optical region 25 and 31 of the lens 20 may be formed to be of any suitable configuration. As shown most clearly in FIG. 2, both the central portions 25 and 31 have a planar bottom surface and a convex upper surface. The central portion 25 has a focal length which is different from the focal length of the second section 31, thereby forming a bifocal lens. It is of course understood that the central portion 25 may have a focal length equal to that of the central portion 31, thereby forming a single focal lens. The first section 24 is positioned on one side of a chord 20b of the lens body 21 and the second section 30 is positioned on the other side of the chord 20b. Preferably, as shown in the figures, the chord 20b is a diameter of the lens body 21. The diameter runs along the longitudinal axis 20a. When a bifocal lens is formed as shown in the figures, the adjacent surface 25d will have a height greater than the height of the adjacent surface 31d, thereby forming the offset as most clearly shown in FIG. 2. Preferably, for best results, the images from both central portions should end up in the same plane. That is, the power of the two central portions should be selected so that the image from infinity projecting through the central portion for distance viewing will be focused in the same plane as the image from a close object, being located at standard reading distance, projected through the central portion for reading.

The central sections 25 and 31 have bottom surfaces in the shape of circular segments, and when the chord 20b is along a diameter, the circular segments are of equal size and form a circular optical region for the lens body. However, it is understood that other embodiments of this invention may incorporate segments of unequal size.

A second embodiment of the present invention is shown in FIGS. 5 through 8. An intraocular lens 50 includes an optical lens body, generally designated as 51, and haptic members 52 and 53 cooperatively connected to the lens body 51 by means well known in the art. The lens body 51 includes a first section 54 and a second section 60. The first section 54 has a planar bottom surface 54a, a convex upper surface 54c and an adjacent edge surface 54b normal to the bottom surface 54a. The second section 60 has a planar bottom surface 60a, a convex upper surface 60c and an adjacent edge surface 60b normal to the bottom surface 60a. The first section 54 and second section 60 are relatively rigid and are not foldable.

The first section 54 has a recess 55 formed along its bottom surface 54a and is proximate to and extends to its adjacent edge surface 54b. Similarly, the second section 60 has a recess 65 formed along its bottom surface 60a and is proximate to and extends to its adjacent edge surface 60b. The recesses 55 and 65 preferably extend the entire length of the adjacent edge surfaces 54b and 60b, respectively. A plurality of supplemental recesses 55a are formed in the recess 55 and a plurality of supplemental recesses 65a are formed in the recess 65. As shown in FIG. 5, there are three supplemental recesses 55a and three supplemental recesses 65a. However, it is understood that any suitable number of recesses may be formed. The supplemental recesses 55a and 65a are cylindrical bores and are normal to the bottom surfaces 54a and 60a. The recesses 55a and 65a extend into the first and second sections 54 and 60 to a depth deeper from the bottom surfaces 54a and 60a, respectively than the recesses 55 and 65. The supplemental recesses 55a and 65a are formed completely within the first section 54 and second section 60, respectively.

The haptic member 52 and first section 54 are formed as an integral one-piece structure by a compression molding and machining process. Similarly, the haptic member 53 and second section 60 are formed as an integral one-piece structure by a compression molding and machining process. However, it will be also appreciated that both one-piece structures may also be produced by other suitable methods such as injection molding or lathing. The first section 54 and second section 60 are made of a biologically tolerable and optically suitable material such as PMMA. The haptic members 52 and 53 may be made of a flexible, compressible, resilient material such as PMMA or polypropylene, or other materials as well known in the art.

A hinge 75 resiliently cooperatively connects the first section 54 to the second section 60. The first section 54 is foldable with respect to the second section 60, wherein the lens body 51 may be folded from an operational configuration, as shown in FIGS. 5, 6 and 7, to a smaller insertion configuration, as shown in FIG. 8, making implantation possible through a smaller cut in the cornea of the eye than would otherwise be possible, and after insertion and upon release of the resilient connecting means the lens body 51 returns to the operational configuration without further manipulation.

The hinge 75 is positioned in recesses 55 and 65. Again, the hinge 75 is of a suitable material such a silicone rubber and preferably Silastic 382 medical grade elastomer. The silastic elastomer has no shrinkage when it cures, which is important in adhering the rubber to the lens. The sections 54 and 60 are placed such that the adjacent edge surfaces 54b and 60b are adjacent and mating as shown in FIGS. 5 and 7. They are then placed in a suitable fixture such that the silicone rubber, or other suitable material, may be molded to form the resilient, foldable hinge 75. The uncured rubber, along with its catalyst, is injected into the recess 55 and 65, as well as supplemental recesses 55a and 65a where it cures to the shape to conform to the recesses 55 and 65 and the supplemental recesses 55a and 65a, as shown in FIGS. 6 and 8, in approximately 20 minutes. A full cure will be affected in approximately 24 hours. Because of the lack of shrinkage of the elastomer as it cures, a tighter friction fit between the rubber and the lens is obtained. The use of the supplemental recesses 55a and 65a assist in keeping the hinge 75 firmly in place in the recesses 55 and 65. An additional friction fit in the supplemental recess 55a and 65a may be obtained by utilizing grooves or spirals within the supplemental recesses. The bottom surface of the hinge 75 is coplanar with the bottom surfaces 54a and 60a when in the operational configuration. The hinge 75 is formed within the first and second sections 54 and 60.

When implanting the intraocular lens 50 into the eye, the first section 54 is folded in a position overlying the second section 60, as shown in FIG. 8. In such a configuration, the adjacent edge surfaces 54b and 60b are coplanar. This enables the lens to be implanted through a smaller cut in the cornea of the eye than would otherwise be possible. After the lens 20 is inserted into the cornea of the eye, it may be released and the resilient hinge 75 returns the lens 50 to its operational configuration as shown in FIGS. 5, 6 and 7, without further manipulation. Because of the resilient nature of the hinge 75, the first section 54 and second section 60 will move from the insertion configuration, as shown in FIG. 8, to the operational configuration as shown in FIGS. 5 and 7. The eye will not see the line created by the hinge 75. It is believed that the hinge 75 will not be seen because of the fact that the sharp image created by the remainder of the central portion by the first section 54 and second section 60 will overpower any blurred edges created by the hinge 75. Further, the use of the hinge along the axis of the lens where the two sections meet will eliminate glare along that section of the lens.

When in the insertion configuration as shown in FIG. 8, the hinge 75 will be bent along its central region creating a circular protrusion 75a. This protrusion is formed along the length of the hinge 75.

The optical region 54 and 60 of the lens 50 may be formed to be of any suitable configuration. As shown most clearly in FIG. 6, both the first section 54 and second section 60 have a planar bottom surface and a convex upper surface. The first section 54 has a focal length which is different from the focal length of the second section 60, thereby forming a bifocal lens. It is of course understood that the first section 54 may have a focal length equal to that of the second section 60, thereby forming a single focal lens. The first section 54 is positioned on one side of a chord 50b of the lens body 51 and the second section 60 is positioned on the other side of the chord 50b. Preferably, as shown in the figures, the chord 50b is a diameter of the lens body 51. The diameter runs along the longitudinal axis 50a. When a bifocal lens is formed as shown in the figures, the adjacent surface 54b will have a height greater than the height of the adjacent surface 60b, thereby forming the offset as most clearly shown in FIG. 6. Preferably, for best results, the images from both central portions should end up in the same plane. That is, the power of the two central portions should be selected so that the image from infinity projecting through the central portion for distance viewing will be focused in the same plane as the image from a close object, being located at standard reading distance, projected through the central portion for reading.

The sections 54 and 60 have bottom surfaces in the shape of circular segments, and when the chord 50b is along a diameter, the circular segments are of equal size and form a circular optical region for the lens body.

A third embodiment is shown in FIGS. 9 through 12. An intraocular lens 80 has an axis 80a and includes an intraocular lens body, generally designated as 81 and two haptic members 82 and 83. The haptic members 82 and 83 are cooperatively connected to the lens body 81 by means well known in the art. The lens body 81 includes a first section, generally designated as 84 and a second section, generally designated as 90. The first section 84 includes an optical region or central portion 85, having a planar bottom surface 85a and convex upper surface 85e. The first section 84 also has a first flange section having a first component 86, having a planar bottom surface 86a and planar upper surface 86e, cooperatively connected to the first end 85b of the central portion 85 and a second component 87, having a planar bottom surface not seen, but similar to surface 86a and planar upper surface 87e, cooperatively connected to a second end 85c of the central portion 85. The second section 90 includes an optical region or central region 91 having a planar bottom surface 91a and a convex upper surface 91e. The second section flange which is cooperatively connected to the central section 91 has a first component 92, having a planar bottom surface 92a and a planar upper surface 92e, which is cooperatively connected to the first end 91b of central section 91 and a second component 93, having a planar bottom surface 93a and a planar upper surface 93e, is cooperatively connected to the second end 91c of central section 91. The central portion 85 has an adjacent edge surface 85d normal to the bottom surface 85a which, when in an operational configuration, is adjacent the adjacent surface edge 91d of the central section 91 which is normal to the bottom surface 91a.

Each of the components 86, 87, 92, and 93 has a bore 86b, 87b, 92b and 93b respectively formed therein normal to the axis 80a. Each of the bores 86b, 87b, 92b and 93b has an access slot 86c, 87c, 92c and 93c respectively on the upper surfaces 86e, 87e, 92e and 93e opening into their respective bores. The access slots 86c, 87c, 92c and 93c are parallel to and overlying the full length of bores 86b, 87b, 92c and 93c. The access slots 86c, 87c, 92c and 93c have a longitudinal opening having a size $H_1$. Each of the bores has at its largest opening a size $H_2$. $H_1$ is sized smaller than $H_2$. Bores 86b and 92b are in general alignment as are bores 87b and 93b when in the operational configuration. The first section 84 is cooperatively connected to the second section 90 by means of resilient strips 100 and 105. The first strip 100 resiliently cooperatively connects the first component 86 to the third component 92 and the second strip 105 resiliently cooperatively connects the second component 87 to the other second component 93. The first section 84 is foldable with respect to the second section 90, wherein the lens body 81 may be folded from an operational configuration to a smaller insertion configuration making implantation possible through a smaller cut in the cornea of the eye than would otherwise be possible and after insertion and upon release of the resilient strips 100 and 105 the lens body 81 returns to the operational configuration without further manipulation. The first section 84 and second section 90 are relatively rigid and are not foldable.

In a preferred embodiment, the haptic member 82, central portion 85 and first and second flange components 86 and 87 are formed as an integral one-piece structure by a compression molding and machining process, as is the haptic member 83, central portion 91 and first and second flange components 92 and 93. However, it will be appreciated that both may be also produced by other suitable methods such as injection molding or lathing. The first section 84 and second section 90 are made of a biological tolerable and optically suitable material such as PMMA. The haptic members 82 and 83 may be made of a flexible, compressible, resilient material such as PMMA or polypropylene, or other materials as well known in the art. The foldable, flexible, resilient strips 100 and 105 may be made of any suitable material such as silicone rubber, and preferably Silastic 382 medical grade elastomer. The resilient strips 100 and 105 each have a width, which when stretched along its length is less than their width when unstretched. When stretched, the strips will increase in length and decrease in width. To cooperatively connect the first section 84 and second section 90, the adjacent surfaces 85d and 91d are positioned such that they are adjacent and mating and the bottom surfaces 85a and 91a coplanar, as in the operational configuration. The stretched strips 100 and 105 are stretched along their longitudinal axis and inserted through the access slots 86c-92c and 87c-93c respectively. The stretched strips 100 and 105 have a length greater than the length of the combined bores 86b and 92b or 87b and 93b. The strips 100 and 105 are then released and they shorten in length and expand in width, thereby substantially filling the bores 86b, 87b, 92b and 93b, thereby creating a friction fit between the bores and the strips. The ends 100a and 105a of strips 100 and 105 respectively are also larger than the bores 86b, 87b, 92b and 93b. This is clearly shown in the figures, especially FIG. 9. The enlarged ends 100a and 105a also serve to assist in holding the resilient strips 100 and 105 in position within the bores.

When implanting the intraocular lens 80 into the eye, the first section 84 is folded in a position overlying the second section 90, as shown in FIG. 12. This enables the lens to be implanted through a smaller cut in the cornea of the eye than would otherwise be possible. After the lens 80 is inserted into the cornea of the eye, it may be released and the resilient strips 100 and 105 return the lens 80 to its operational configuration, as shown in FIGS. 9 and 11, without further manipulation. Because of the resilient nature of the strips 100 and 105, the first section 84 and second section 90 will move from the insertion configuration as shown in FIG. 12 and move to the operational configuration as shown in FIGS. 9 and 11. When in the operational configuration, the bottom surfaces 85a and 91a are coplanar. For reasons similar to that discussed with respect to the first embodiment, the eye will not see the line created by the adjacent surfaces 85d and 91d.

The optical region 85 and 91 of the lens 80 may be formed to be of any suitable configuration. As shown most clearly in FIG. 10, both the central portions 85 and 91 have a planar bottom surface and a convex upper surface. The central portion 85 has a focal length which is different from the focal length of the second section 91, thereby forming a bifocal lens. It is of course understood that the central portion 85 may have a focal length equal to that of the central portion 91, thereby forming a single focal lens. The first section 84 is positioned on one side of a chord 80b of the lens body 81 and the second section 90 is positioned on the other side of the chord 80b. Preferably, as shown in the figures, the chord 80b is a diameter of the lens body 81. The diameter runs along the longitudinal axis 80a. When a bifocal lens is formed as shown in the figures, the adjacent surface 85d will have a height greater than the height of the adjacent surface 91d, thereby forming the offset as most clearly shown in FIG. 10. Preferably, for best results, the images from both central portions should end up in the same plane. That is, the power of the two central portions should be selected so that the image from infinity projecting through the central portion for distance viewing will be focused in the same plane as the image from a close object, being located at standard reading distance, projected through the central portion for reading.

The central sections 85 and 91 have bottom surfaces in the shape of circular segments, and when the chord 80b is along a diameter, the circular segments are of equal size and form a circular optical region for the lens body.

Other modifications of the invention will be apparent to those skilled in the art in light of the foregoing description. This description is intended to provide specific examples of individual embodiments which clearly disclosed the present invention. Accordingly, the invention is not limited to these embodiments or to the use of elements having specific configurations and shapes as presented herein. All alternative modifications and variations of the present invention which follows in the spirit and broad scope of the appended claims are included.

What is claimed is:

1. A bifocal intraocular lens adapted for use as an artificial lens implant, said intraocular lens comprising:
   (a) optical lens body having a chord and having separate first and second relatively rigid sections;
   (b) said first section positioned on one side of said chord and said second section on the other side of said chord; and
   (c) said first section having a focal length and said second section having a focal length different from said focal length of said first section;
   (d) said first section having a central portion and an outwardly extending flange portion, said central and flange portions having bottom surfaces, said flange portion of said first section has a first component cooperatively connected to a first end of said central portion and a second component cooperatively connected to a second end of said central portion;
   (e) said second section having a central portion and an outwardly extending flange portion, said central and flange portions having bottom surfaces, said flange portion of said second section has a first component cooperatively connected to a first end of said central portion and a second portion cooperatively connected to a second end of said central portion and
   (f) means for resiliently cooperatively connecting said flange portions of said first and second sections, said first section foldable with respect to said second section, wherein said lens body may be folded from an operational configuration to a smaller insertion configuration making implantation possible through a smaller cut in the cornea of the eye than would otherwise be possible and after insertion and upon release of said connecting means said lens body returns to said operational configuration without further manipulation.

2. The intraocular lens of claim 1, wherein said connecting means encapsulates said flange portions and said connecting means has a bottom surface that does not extend below said bottom surface of said central portions when in said operational configuration.

3. The intraocular lens of claim 2, wherein said bottom surface of said connecting means is coplanar with said bottom surfaces of said central portion when in said operational configuration and when in said insertion configuration one of said bottom surfaces is overlying the other of said bottom surfaces.

4. The intraocular lens of claim 3, wherein said connecting means has a thickness proximate a central region where said first and second sections are adjacent that is less than its thickness at its periphery.

5. The intraocular lens of claim 1, wherein said connecting means is a silicone rubber.

6. The intraocular lens of claim 1, wherein said lens body is circular and said chord is a diameter.

7. The intraocular lens of claim 1, further comprising haptic elements cooperatively to said lens body.

8. A bifocal intraocular lens adapted for use as an artificial lens implant, said intraocular lens comprising:
   (a) an optical lens body having a chord and having separate first and second relatively rigid sections, said first and second sections having coplanar bottom surfaces and adjacent edge surfaces;
   (b) said first section positioned on one side of said chord and said second section on the other side of said chord;
   (c) said first section having a focal length and said second section having a focal length different from said focal length of said first section;
   (d) said first section having a first recess in its bottom surface proximate its adjacent edge surface;
   (e) said second section having a second recess in its bottom surface proximate its adjacent edge surface and
   (f) means for resiliently cooperatively connecting said first section to said second section, said first section foldable with respect to said second section, said connecting means being positioned entirely within said first and second recesses and having a bottom surface coplanar with said bottom surfaces of said lens body sections.

9. The intraocular lens of claim 8, wherein said connecting means is silicone rubber molded in said receses.

10. The intraocular lens of claim 8, further comprising supplemental recesses formed in said first and second recesses, said supplemental recesses extending the depth of said recesses wherever said supplemental recesses are formed.

11. The intraocular lens of claims 10, wherein said connecting means is also positioned in said supplemental recesses.

12. The intraocular lens of claim 8, further comprising haptic elements cooperatively connected to said lens body.

13. The intraocular lens of claim 8, wherein said lens body is circular and said chord is a diameter.

14. A bifocal intraocular lens adapted for use as an artificial lens implant, said intraocular lens comprising:
   (a) an optical lens body having a chord and having separate first and second relatively rigid circular segment sections;
   (b) said first section positioned on one side of said chord and said second section on the other side of said chord;
   (c) said first section having a focal length and said second section having a focal length different from said focal length of said first section;
   (d) said first section having a central portion having first and second ends and a first flange portion cooperatively connected to said first end and a second flange portion cooperatively connected to said second end;
   (e) said second section having a central portion having first and second ends and a third flange portion cooperatively connected to said first end and a fourth flange portion cooperatively connected to said second end;
   (f) each of said flange portions having a bore, said bore of said first flange portion in general alignment with said bore of said third flange portion and said bore of said second flange portion in general alignment with said bore of said fourth flange portion when in an operational configuration and
   (g) means extending through said aligned bores to permit folding of said lens body.

15. The intraocular lens of claim 14, further comprising first means for resiliently cooperatively connecting said first flange portion to said third flange portion and a second means for resiliently connecting said second flange portion to said fourth flange portion, said first section foldable with respect to said second section, wherein said lens body may be folded from an operational configuration to a smaller insertion configuration making implantation possible through a smaller cut in the cornea of the eye than would otherwise be possible and after insertion and upon release of said connecting means said lens body returns to said operational configuration without further manipulation.

16. The intraocular lens of claim 14, wherein each of said bores have an access slot opening into said bores, said access slots sized smaller than said bores; and wherein said first connecting means comprises a first resilient strip and said second connecting means comprises a second resilient strip, both of said first and second strips have a width, which when stretched is less than their width when unstretched, whereby said first strip is extended along its longitudinal axis and inserted through said access openings into said bores of said first and third flange portions and then released, expanding in width to substantially fill said bores, and said second strip is extended along its longitudinal axis and inserted through said access openings into said bores of said second and fourth flange portions and then released, expanding in width to substantially fill said bores.

17. The intraocular lens of claim 14, further comprising haptic elements cooperatively connected to said lens body.

18. The intraocular lens of claim 14, wherein said lens body is circular and said chord is a diameter.

* * * * *